United States Patent
Hyde et al.

(10) Patent No.: US 9,443,409 B1
(45) Date of Patent: Sep. 13, 2016

(54) SYSTEMS TO MONITOR PROXIMITY OF BODY PORTIONS RELATIVE TO AN ENVIRONMENT

(71) Applicant: Elwha LLC, Bellevue, WA (US)

(72) Inventors: Roderick A. Hyde, Redmond, WA (US); Jordin T. Kare, San Jose, CA (US); Eric C. Leuthardt, St. Louis, MO (US); Mark A. Malamud, Seattle, WA (US); Tony S. Pan, Bellevue, WA (US); Elizabeth A. Sweeney, Seattle, WA (US); Clarence T. Tegreene, Mercer Island, WA (US); Charles Whitmer, North Bend, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

(21) Appl. No.: 14/665,495

(22) Filed: Mar. 23, 2015

(51) Int. Cl.
*G08B 23/00* (2006.01)
*G08B 21/02* (2006.01)
*G08B 21/18* (2006.01)
*G08B 21/00* (2006.01)

(52) U.S. Cl.
CPC ............ *G08B 21/02* (2013.01); *G08B 21/182* (2013.01)

(58) Field of Classification Search
CPC ................................ G08B 1/02; G08B 21/182
See application file for complete search history.

(56) References Cited

U.S. PATENT DOCUMENTS

| | | | | |
|---|---|---|---|---|
| 8,640,946 B1* | 2/2014 | Block | ................ | G06Q 20/1085 235/379 |
| 8,651,373 B1* | 2/2014 | Block | ................ | G06Q 20/1085 235/379 |
| 9,098,961 B1* | 8/2015 | Block | ................ | G07F 19/201 |
| 2010/0324455 A1 | 12/2010 | Rangel et al. | | |
| 2012/0165759 A1 | 6/2012 | Rogers et al. | | |
| 2013/0041235 A1* | 2/2013 | Rogers | ................ | A61B 5/6867 600/306 |
| 2013/0333094 A1* | 12/2013 | Rogers | ................ | A61B 5/6806 2/161.7 |
| 2014/0001058 A1* | 1/2014 | Ghaffari | ............... | G01N 27/327 205/792 |
| 2014/0081858 A1* | 3/2014 | Block | ................ | G07F 19/207 705/43 |
| 2014/0163439 A1* | 6/2014 | Uryash | ................ | A61B 8/08 601/47 |
| 2014/0171751 A1* | 6/2014 | Sankman | ........... | A61B 5/02055 600/301 |

(Continued)

OTHER PUBLICATIONS

Axisa, F., Brosteaux, D., De Leersnyder, E., Bossuyt, F., Vanfleteren, J., Hermans, B., Puers, R.; Biomedical Stretchable Systems Using Mid Based Stretchable Electronics Technology; Proceedings of the 29th Annual International Conference on the IEEE EMBS Cite International, Lyon, France; Aug. 23-26, 2007; pp. 5687-5690.

(Continued)

*Primary Examiner* — Erin File
(74) *Attorney, Agent, or Firm* — Daniel J. Honz

(57) ABSTRACT

A device embodiment includes, but is not limited to, a deformable substrate; a sensor assembly coupled to the deformable substrate, the sensor assembly including a proximity sensor configured to generate one or more sense signals associated with a proximity of an environmental object relative to the body portion; circuitry operably coupled to the sensor assembly and configured to receive the one or more sense signals and to determine whether the proximity of the environmental object relative to the body portion changes over a time period; and a reporting device operably coupled to the circuitry and configured to generate one or more communication signals associated with one or more of the environmental object or a change in proximity of the environmental object relative to the body portion responsive to instruction by the circuitry.

50 Claims, 8 Drawing Sheets

(56) References Cited

U.S. PATENT DOCUMENTS

| | | | | |
|---|---|---|---|---|
| 2014/0343389 A1* | 11/2014 | Goldstein | ............ | A61B 5/0022 600/383 |
| 2015/0248470 A1* | 9/2015 | Coleman | ............... | G96F 19/363 707/740 |
| 2015/0313498 A1* | 11/2015 | Coleman | ............... | A61B 5/0482 600/383 |
| 2015/0368804 A1* | 12/2015 | Lee | ..................... | C23C 18/1639 264/105 |
| 2015/0373831 A1* | 12/2015 | Rogers | ................. | H01M 10/02 429/121 |
| 2015/0380355 A1* | 12/2015 | Rogers | ................. | H01L 23/538 257/773 |
| 2016/0015280 A1* | 1/2016 | Hyde | ................. | A61B 5/02055 600/301 |
| 2016/0015299 A1* | 1/2016 | Chan | .................... | A61B 5/1116 600/595 |
| 2016/0015972 A1* | 1/2016 | Hyde | ................. | A61N 1/36014 607/48 |

OTHER PUBLICATIONS

Kim, D. et al., Epidermal Electronics, Science, vol. 333 ,838-843 (2011), DOI: 10.1126/science.1206157.

Salvatore, G.A. et al., Wafer-scale design of lightweight and transparent electronics that wraps around hairs, Nature Communications, 5:2982 (2014) | DOI: 10.1038/ncomms3982.

Torpy, J.M., Peripheral Neuropathy; The Journal of American Medical Association; Apr. 21, 2010; vol. 303, No. 15; p. 1.

Wang, C. et al., A Flexible Proximity Sensor Fully Fabricated by Inkjet Printing, Sensors, 10(5) 2010; DOI: 10.3390/s100505054.

Xu, S. et al, Soft Microfluidic Assemblies of Sensors, Circuits, and Radios for the Skin, Science, vol. 344, 70-74 (2014).

Yeo, W. et al., Multifunctional Epidermal Electronics Printed Directly Onto the Skin, Advanced Materials vol. 25(20), 2773-2778 (2013).

Ying, M. et al., Silicon nanomembranes for fingertip electronics, Nanotechnology, vol. 23, No. 34, 1-7 (2012).

\* cited by examiner

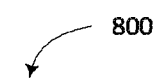

| 802 | DETECTING A PROXIMITY OF AN ENVIRONMENTAL OBJECT RELATIVE TO A BODY PORTION |

| 804 | DETECTING ONE OR MORE OF A SPEED, A VELOCITY, OR AN ACCELERATION OF AT LEAST ONE OF THE BODY PORTION OR THE ENVIRONMENTAL OBJECT |

| 806 | DETERMINING WHETHER THE BODY PORTION OR THE ENVIRONMENTAL OBJECT IS IN MOTION BASED ON ONE OR MORE OF THE SPEED, THE VELOCITY, OR THE ACCELERATION OF THE BODY PORTION OR THE ENVIRONMENTAL OBJECT |

| 808 | WHEN THE BODY PORTION OR THE ENVIRONMENTAL OBJECT IS DETERMINED TO BE IN MOTION, GENERATING ONE OR MORE COMMUNICATION SIGNALS BASED ON DETECTION OF THE PROXIMITY OF THE ENVIRONMENTAL OBJECT RELATIVE TO THE BODY PORTION |

FIG. 8

902 DETECTING A PROXIMITY OF AN ENVIRONMENTAL OBJECT RELATIVE TO A BODY PORTION

904 DETECTING A SECOND PROXIMITY OF THE ENVIRONMENTAL OBJECT RELATIVE TO THE BODY PORTION

906 DETERMINING WHETHER THE FIRST PROXIMITY OF THE ENVIRONMENTAL OBJECT RELATIVE TO THE BODY PORTION DIFFERS FROM THE SECOND PROXIMITY OF THE ENVIRONMENTAL OBJECT RELATIVE TO THE BODY PORTION

908 WHEN THE FIRST PROXIMITY OF THE ENVIRONMENTAL OBJECT RELATIVE TO THE BODY PORTION IS DETERMINED TO DIFFER FROM THE SECOND PROXIMITY OF THE ENVIRONMENTAL OBJECT RELATIVE TO THE BODY PORTION, GENERATING ONE OR MORE COMMUNICATION SIGNALS BASED ON DETECTION OF AT LEAST ONE OF FIRST PROXIMITY OR THE SECOND PROXIMITY

FIG. 9

SYSTEMS TO MONITOR PROXIMITY OF BODY PORTIONS RELATIVE TO AN ENVIRONMENT

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)).

Priority Applications:
None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a device includes, but is not limited to: a deformable substrate configured to conform to a skin surface of a body portion; a sensor assembly coupled to the deformable substrate, the sensor assembly including a proximity sensor configured to generate one or more sense signals associated with a proximity of an environmental object relative to the body portion; circuitry operably coupled to the sensor assembly and configured to receive the one or more sense signals associated with the proximity of an environmental object relative to the body portion and to determine whether the proximity of the environmental object relative to the body portion changes over a time period; and a reporting device operably coupled to the circuitry and configured to generate one or more communication signals responsive to instruction by the circuitry, the one or more communication signals associated with one or more of the environmental object or a change in proximity of the environmental object relative to the body portion.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 8 is a flowchart of a method of monitoring proximity of body portions relative to an environment.

FIG. 9 is a flowchart of a method of monitoring proximity of body portions relative to an environment.

DETAILED DESCRIPTION

Figure 1:
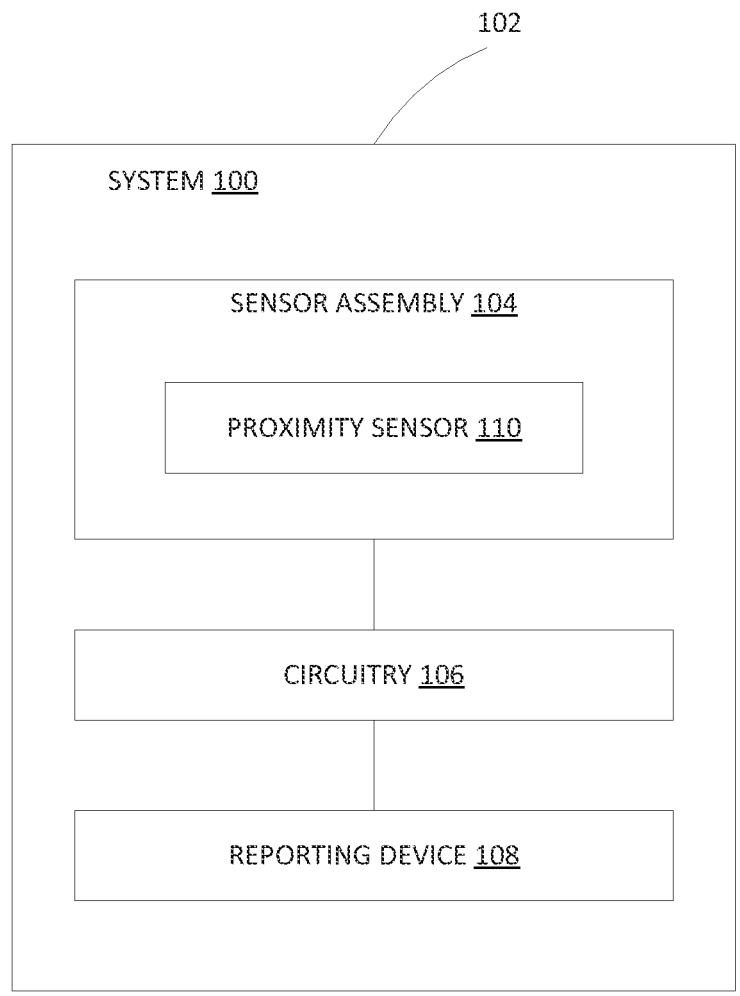
FIG. 1 is a schematic of a device for monitoring proximity of body portions relative to an environment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Systems are described for monitoring environmental conditions around extremities to aid in preventing damage associated with physical impact, such as tissue and nerve damage. Such systems can monitor the environment in proximity to body portions of an individual to identify potential hazards for collision with the body portion, such as environmental objects in proximity to the body portion. For example, the individual can be an individual afflicted with neuropathy, an individual in a medical facility, an individual with visual impairments that reduce their ability to acknowledge environmental conditions while physically maneuvering about the environment, an individual that negotiates dark environments (e.g., wakes and moves about at night), and so forth. Individuals afflicted with neuropathy (e.g., peripheral neuropathy) may have reduced capabilities to detect when a body portion comes in contact with another object or a surface due to an impairment of sensation, movement, or other normal body functions. Neuropathy can result from a disease, such as diabetes or immune system diseases, from interactions with various medications or medical treatments (such as chemotherapy), from inherited characteristics, from vitamin deficiency, from traumatic injury, from excessive alcohol usage, from infections (e.g., human immunodeficiency virus (HIV)), or other conditions and sources (see e.g., Torpy, Peripheral Neuropathy, JAMA, Vol. 303 (15), 1556 (April 2010), which is incorporated herein by reference). In an embodiment, the systems and devices described herein may be used to monitor for environmental objects in physical proximity to body portions on which the systems/devices are positioned. When an environmental object is sensed, the systems/devices report information including, but not limited to, information associated with the environmental object (e.g., a hardness of the object) and a proximity of the environmental object. The report can provide an indication of a warning of imminent impact, a warning of proximity, an estimated time of impact, an estimated force of impact, and so forth. The systems and devices can be configured to take proximity measurements and to report information based on whether the systems and devices are in motion.

In embodiments, the systems and devices described herein employ a sensor assembly having at least one proximity sensor to monitor for environmental objects in proximity to the body portion on which the sensor assembly is positioned and to generate one or more sense signals in response thereto. The proximity sensor can include, but is not limited to, one or more of an optical sensor, an acoustic sensor, or an electromagnetic proximity sensor. The systems described herein can include circuitry configured to receive the one or more sense signals from the sensor assembly associated with a proximity of an environmental object relative to the body portion. The circuitry can be configured to determine whether to actuate the reporting device based on the one or more sense signals from the sensor assembly, such as dependent on whether the sense signals provide an indication of imminent impact, dependent on whether the body portion is in motion, and so forth.

In embodiments, the systems and devices described herein employ a reporting device configured to generate one or more communication signals responsive to instruction by the circuitry. The reporting device can convey various communications, including but not limited to, information associated with the environmental object, a proximity of the environmental object relative to the body portion, and so forth. In embodiments, the reporting device is configured to provide one or more of an auditory indication of the information, a visual indication of the information, or a tactile indication of the information.

In an embodiment, shown in FIG. 1, a system (or device) 100 is configured to monitor environmental conditions proximate to a body portion on which the system 100 is positioned, such as to identify environmental objects in proximity to the body portion to aid in preventing damage associated with physical impact between the environmental object and the body portion. Such monitoring can initiate after occurrence of one or more predetermined events, such as after an extremity with peripheral neuropathy has begun to move. The system 100 includes a substrate 102, a sensor assembly 104, circuitry 106, and a reporting device 108. In embodiments, the system 100 includes one or more epidermal electronic systems (EES) to monitor physiological, positional, and movement conditions for determining one or more of a proximity of an environmental object relative to the body portion, a motion of the body portion, a type of object in proximity to the body portion, or so forth. EES describe classes of electronic systems that provide thicknesses, effective elastic moduli, and flexibility suitable for conforming to and interfacing with a skin surface (see, e.g., Kim et al., Epidermal Electronics, Science, Vol. 333, 838-843 (2011) and Yeo et al., Multifunctional Epidermal Electronics Printed Directly Onto the Skin, Advanced Materials Vol. 25(20), 2773-2778 (2013), which are incorporated herein by reference), and can incorporate sensors (e.g., physiological, temperature, strain) and associated circuitry (e.g., transistors, diodes, photodetectors, radio frequency components, capacitors, oscillators).

The substrate 102 is a deformable (e.g., flexible, stretchable) substrate configured to interface with, and conform to, a skin surface of a subject. The deformable and conformable nature of the substrate 102 facilitates interaction/interfacing with the skin surface, a generally low-modulus and deformable natural surface. For example, the substrate 102 can include one or more of an elastomeric polymer, a hydrocolloid film, a nanomembrane (e.g., silicon nanomembrane), or other deformable material. In embodiments, the substrate 102 can include one or more coating. The substrate 102 can be positioned in proximity with the skin surface according to various mechanisms including, but not limited to, affixed to the skin via an adhesive material, held in place by an external pressure, such as pressure provided by a material wrapped around or about the body portion (e.g., a fabric, a garment, a bandage, etc.), and so forth. In embodiments, the substrate 102 is configured to reversibly deform to coordinate with a deformation of the skin surface of the body portion upon which the substrate 102 is mounted or positioned. For example, the substrate 102 can conform to the skin surface during a deformation of the skin surface, during a rest state of the skin surface, and so forth. In an embodiment, the substrate 102 includes a gas-permeable elastomeric sheet on which electronic components of an EES reside (see, e.g., Kim et al., incorporated herein by reference), including, but not limited to, one or more of the sensor assembly 104, the circuitry 106, or the reporting device 108. In an embodiment, the substrate 102 includes a microfluidic enclosure defined by opposing structured elastomeric substrates, between which electronic components of an EES reside (see e.g., Xu et al, Soft Microfluidic Assemblies of Sensors, Circuits, and Radios for the Skin, Science, Vol. 344, 70-74 (2014), which is incorporated herein by reference).

Figure 2:
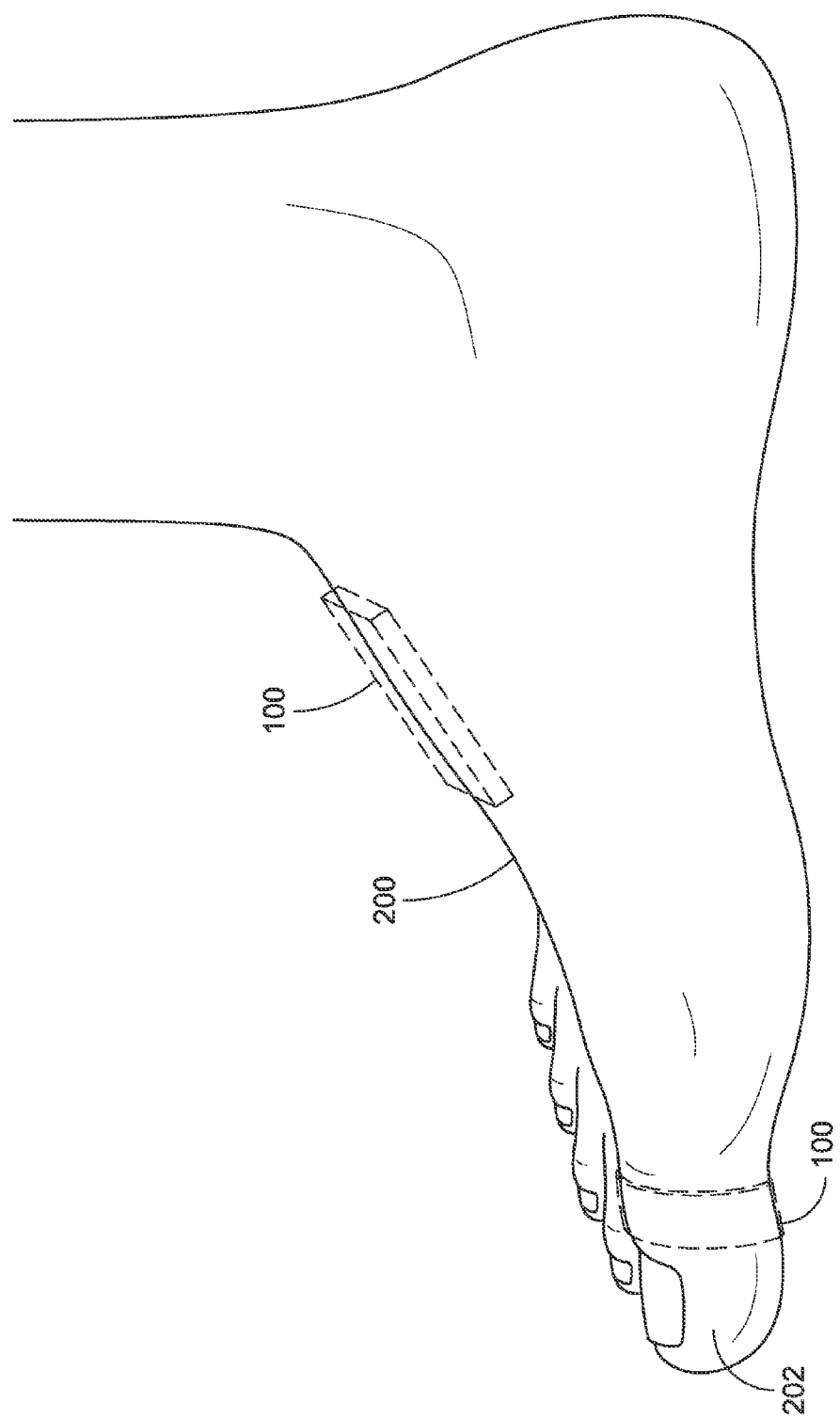
FIG. 2 is a schematic of an embodiment of a device such as shown in FIG. 1.

The substrate 102 can also be configured for interaction with a skin surface of a particular body portion. In example embodiments, the body portion includes one or more of a finger, a hand, a wrist, a toe, a foot, an ankle, an arm, an elbow, a leg, a knee, a shoulder, a hip, a spinal portion (e.g., a region proximate to one or more of a cervical spine, a thoracic spine, a lumbar spine, a sacral spine, or a coccygeal spine), a rib portion (e.g., a region proximate to a rib, such as where the rib attaches the spine), a torso, a neck, or a head region (e.g., face, scalp). For example, the substrate 102 can conform to or be formed as a tubular structure to facilitate interaction with a finger or toe, such as being wrapped around at least a portion of the finger or toe (see, e.g., Ying et al., Silicon nanomembranes for fingertip electronics, Nanotechnology, Vol. 23, No. 34, 1-7 (2012), which is incorporated herein by reference; Kim et al., ibid.; Yeo et al., ibid.). In an embodiment, shown in FIG. 2, the system 100 is positioned on a foot 200 of the subject for monitoring environmental conditions around the foot 200 or other body portion in proximity to the foot 200 to detect environmental objects in proximity to the foot 200 to avoid injury (e.g., tissue damage, nerve damage, and so forth) based on collision or impact between the foot 200 and the environmental objects. FIG. 2 also shows the system 100 wrapped around an individual toe 202 of the foot 200, where the system 100 can monitor the toe 202, such as one with diabetic neuropathy. In an implementation, the system 100 is associated with a patient afflicted with neuropathy, due to diabetes or other cause, where one or more devices 100 are configured to conform around each of one or more toes of the patient to monitor for environmental objects in proximity to each respective toe. In embodiments, the system 100 is configured to identify other body portions (such as another toe, finger, and the like), and distinguish between the other body portions and environmental objects. For example, the system 100 can identify an object in proximity to the system 100 as being a body portion other than that on which the system 100 is positioned, such that the other body portion is not a threat for impact with the body portion on which the system 100 is positioned. For instance, when the system 100 is positioned on the toe 202, the system 100 can recognize that a different toe on foot 200, while being in close proximity to the system 100, is not a threat for impact with the toe 202 on which the system 100 is positioned. Such a determination can be facilitated by a sensor of the sensor assembly 104, described further herein.

In embodiments, the system 100 is configured to be disposable, such that the individual on which the system 100 is positioned (or other individual, such as a healthcare worker caring for the individual) can remove the system 100 for disposal and introduce a new system 100 for positioning on the body portion. In embodiments, the system 100 is reusable, such that after removing the system 100 from interaction with the body portion, the system 100 can be replaced on the same or different body portion for usage to monitor the environment about the body portion for environmental objects that could pose a threat for physical impact with the body portion.

The physical impact with the body portion can result from the individual moving their body into contact with the environmental object, such as an individual moving their foot and stubbing their toe on a piece of furniture, moving the body portion into contact with a floor surface or foreign object on a floor surface, and so forth; can result from an environmental object falling onto the body portion; or other impact-based interactions. Where an individual is affected by neuropathic condition, such as peripheral neuropathy, the individual may not recognize that an impact is imminent, and may not recognize or feel that an impact has occurred to a particular body portion. The system 100 can be configured to monitor the environmental conditions and report information to one or more of the individual, a healthcare professional, or a healthcare network, where the information can be one or more of information associated with an environmental object, information associated with a proximity of the environmental object relative to the body portion, an estimated time of impact, an estimated force of impact, or so forth.

Figure 3:
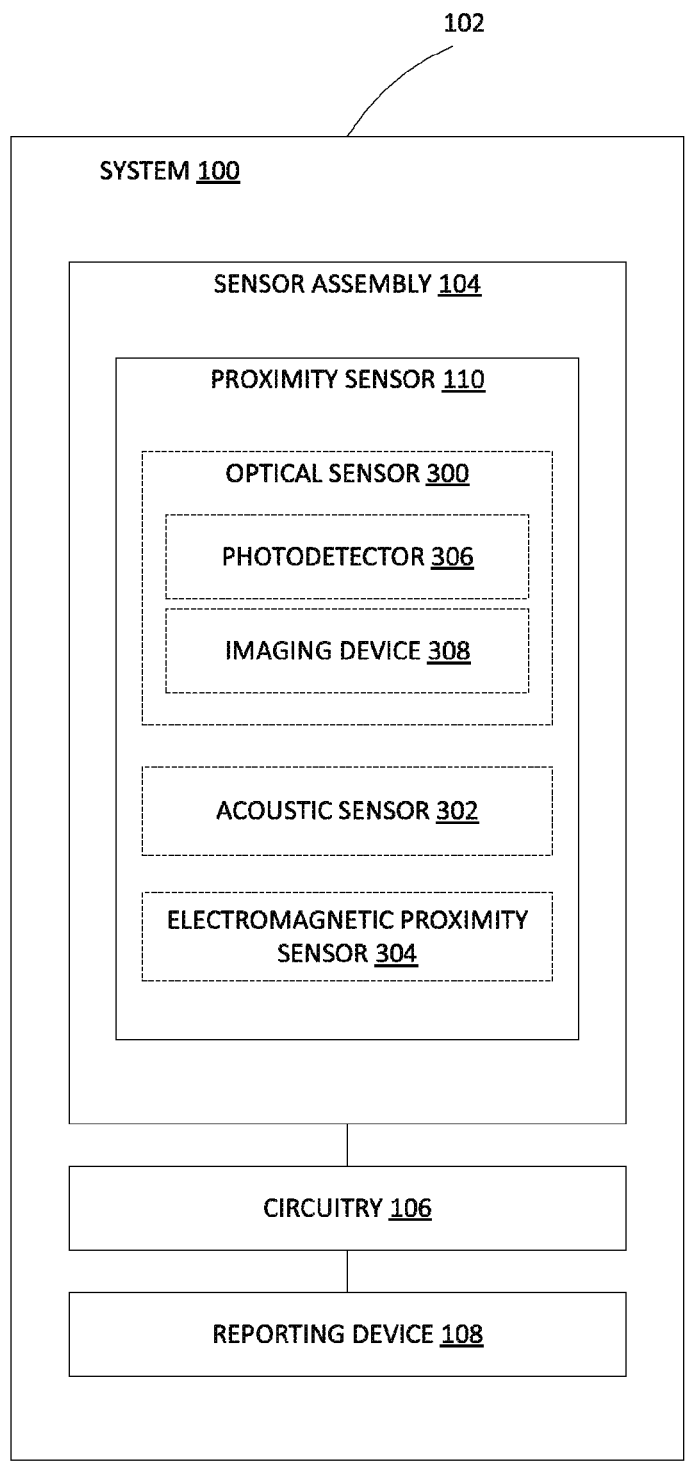
FIG. 3 is a schematic of an embodiment of a device such as shown in FIG. 1.

In embodiments, the sensor assembly 104 is coupled to the deformable substrate 102 and includes a proximity sensor 110 configured to generate one or more sense signals associated with a proximity of an environmental object relative to the body portion. For example, the proximity sensor 110 can measure a change in proximity over time between the system 100 (and corresponding body portion to which the system 100 is mounted) and the environmental object or surface, where the absolute proximity, rate of change in proximity, or relative change in proximity can be utilized to correlate to information related to a probable impact between the body portion and the environmental object or surface. The circuitry 106 (e.g., electric circuitry) is configured to receive the sense signals from the sensor assembly 104 (e.g., the sense signals from the proximity sensor 110) for processing, such as to determine whether the sense signals are indicative of an environmental object, a type of environmental object, and so forth. In embodiments, the sensor assembly 104 can detect whether the system 100 is being worn by a user. For example, the sensor assembly 104 can utilize one or more of a motion sensor, an accelerometer, a temperature sensor, a pressure sensor, or so forth, to determine contact between the system 100 and the subject. In embodiments, referring to FIG. 3, the proximity sensor 110 includes one or more of an optical sensor 300, an acoustic sensor 302, or an electromagnetic proximity sensor 304.

The optical sensor 300 is configured to detect one or more optical signals (e.g., one or more optical electromagnetic signals) and generate one or more sense signals in response thereto. The optical sensor 300 can detect and identify environmental objects and their proximity relative to the system 100 based on the detected optical signals. In embodiments, the circuitry 106 is configured to determine one or more of a proximity of the environmental object relative to the system or an identity of the environmental object based on the sense signals from the optical sensor 300. In embodiments, the optical sensor 300 includes one or more of a photodetector 306 or an imaging device 308. In embodiments, the photodetector 306 is configured to detect one or more electromagnetic signals reflected from a surface of an environmental object in order to detect a proximity of the object relative to the system 100. The origin of the electromagnetic signals can include the optical sensor 300, or other component of the system 100. In embodiments, the proximity sensor 110 is configured to detect nearby objects based on signals emitted from the objects, such as radiant energy (e.g., heat from objects, persons, animals, or so forth). For example, the proximity sensor 110 can include one or more of a bolometer or a thermal imaging device to measure incident electromagnetic radiation of objects in proximity to the system 100. In embodiments, the circuitry 106 is configured to determine one or more of a proximity of the environmental object relative to the system or an identity of the environmental object based on the output from the proximity sensor (e.g., the photodetector 306, the imaging device, or so forth). In embodiments, the imaging device 308 includes a camera configured to generate a visual image of one or more electromagnetic objects in proximity to the system 100. In embodiments, the circuitry 106 is configured to determine one or more of a proximity of the environmental object relative to the system or an identity of the environmental object based on the visual image.

The acoustic sensor 302 is configured to detect one or more acoustic signals and generate one or more sense signals in response thereto. The acoustic sensor 302 can detect and identify environmental objects and their proximity relative to the system 100 based on the detected acoustic signals. In embodiments, the circuitry 106 is configured to determine one or more of a proximity of the environmental object relative to the system or an identity of the environmental object based on the sense signals from the acoustic sensor 302. In embodiments, the acoustic sensor 302 is configured to detect one or more ultrasonic signals, such as an ultrasonic signal reflected from a surface of an environmental object. The origin of the ultrasonic signal can include the acoustic sensor 302, or other component of the system 100. In embodiments, the acoustic sensor 302 is configured to detect one or more radio-frequency signals, such as a radio-frequency signal reflected from a surface of an environmental object. The origin of the radio-frequency signal can include the acoustic sensor 302, or other component of the system 100. In embodiments, the circuitry 106 is configured to identify or categorize the environmental object based on received sense signals from the acoustic sensor 302. For example, the sense signals from the acoustic sensor 302 can provide an indication of elasticity, hardness, or other characteristic of a sensed object to classify a sensed object (e.g., an environmental object, a biological object, a hard surface, a soft surface), to distinguish one sensed object from another object (e.g., an environmental object versus a biological object, a hard object versus a soft object), and so forth.

The electromagnetic proximity sensor 304 is configured to generate one or more electromagnetic signals and to detect one or more of the electromagnetic signals reflected from a surface (e.g., a surface of an environmental object, a surface of a biological object). The electromagnetic proximity sensor 304 is configured to generate one or more sense signals in response to the detected electromagnetic signals for receipt by the circuitry 106. The electromagnetic proximity sensor 304 can detect and identify environmental objects and their proximity relative to the system 100 based on the detected electromagnetic signals, such as those reflected from a surface of an environmental object. In embodiments, the circuitry 106 is configured to determine one or more of a proximity of the environmental object relative to the system or an identity of the environmental object based on the sense signals from the electromagnetic proximity sensor 304.

Figure 4:
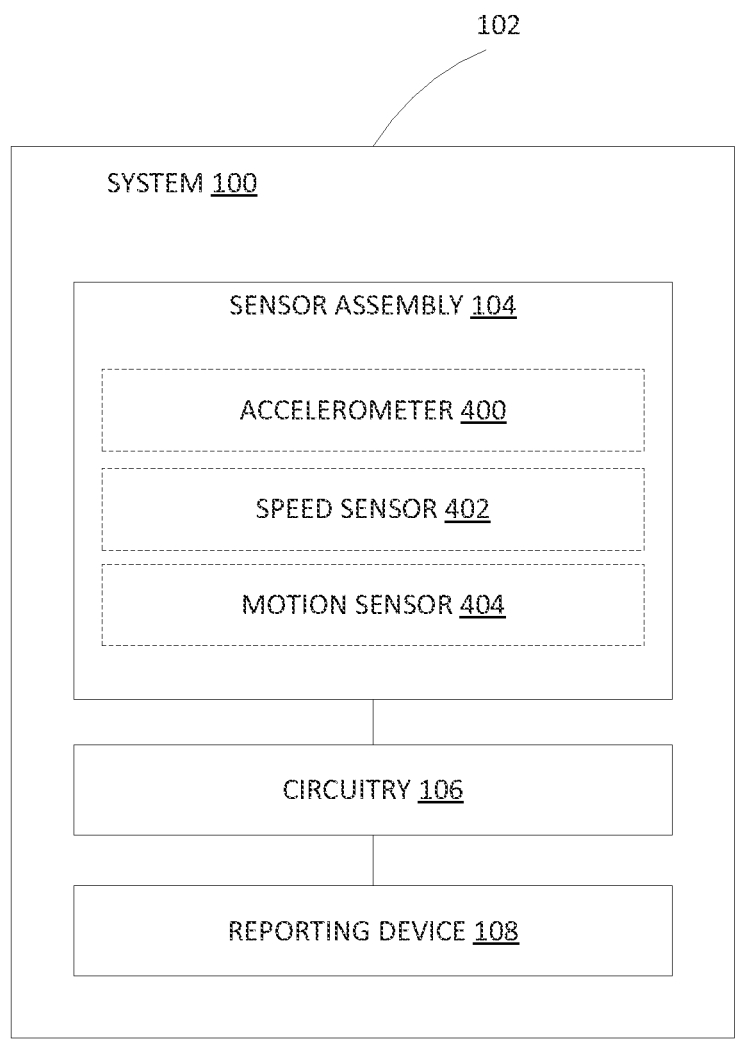
FIG. 4 is a schematic of an embodiment of a device such as shown in FIG. 1.

In embodiments, one or more components of the system 100 can operate or activate based on motion of the system 100, which corresponds to motion of the body portion (e.g. foot 200) due to positioning or mounting of the system 100 to the body portion. For example, the opportunity or risk of physical impact to the body portion can occur during movement of the body portion, since the individual will be moving relative to the environment and objects associated with the environment. In embodiments, such as shown in FIG. 4, the sensor assembly 104 includes one or more of an accelerometer 400, a speed sensor 402, or a motion sensor 404. The accelerometer 400 is configured to measure an acceleration of the body portion. In embodiments, the acceleration of the body portion measured by the accelerometer 400 is utilized, such as by the circuitry 106, to measure or determine one or more of motion of the body portion, vibration of the body portion, orientation of the body portion, or so forth. In embodiments, the circuitry 106 is configured to actuate the proximity sensor 110 responsive to the acceleration of the body portion. For instance, the circuitry 106 may engage the proximity sensor 110 to begin monitoring the environment for environmental objects based on acceleration of the body portion, which can provide an indication of movement of the body portion, to aid in preventing collisions between the body portion and the environmental objects. In embodiments, the circuitry 106 is configured to determine an estimated time of impact of the body portion and an environmental object based on the signals generated by the proximity sensor 110 and the acceleration of the body portion determined by the accelerometer 400. In embodiments, the circuitry 106 is configured to determine an estimated force of impact of the body portion and an environmental object based on the signals generated by the proximity sensor 110 and the acceleration of the body portion determined by the accelerometer 400.

The speed sensor 402 is configured to measure at least one of a speed or a velocity of the body portion. For example, in embodiments, the speed sensor 402 is configured to measure at least one of a speed of the body portion relative to a reference point in the environment or a velocity of the body portion relative to a reference point in the environment. In embodiments, the reference point in the environment is an environmental object detected by the system 100. In embodiments, the speed sensor 402 includes one or more of a lasing component for speed measurements, a piezoelectric component for speed measurements, an optical component for speed measurements, or so forth. In embodiments, the circuitry 106 is configured to actuate the proximity sensor 110 responsive to the speed or velocity of the body portion. For instance, the circuitry 106 may engage the proximity sensor 110 to begin monitoring the environment for environmental objects based on a speed or velocity of the body portion, which can provide an indication of movement of the body portion, to aid in preventing collisions between the body portion and the environmental objects. In embodiments, the circuitry 106 is configured to determine an estimated time of impact of the body portion and an environmental object based on the signals generated by the proximity sensor 110 and the speed or velocity of the body portion determined by the speed sensor 402. In embodiments, the circuitry 106 is configured to determine an estimated force of impact of the body portion and an environmental object based on the signals generated by the proximity sensor 110 and the speed or velocity of the body portion determined by the speed sensor 402.

The motion sensor 404 is configured to detect one or more of a movement of the body portion, a position of the body portion, or aspects associated with movement of an environmental object (e.g., acceleration, velocity, speed of the environmental object, or so forth). In embodiments, detection of the motion of the body portion is utilized as a trigger of when to begin monitoring for environmental objects in proximity to the body portion. In embodiments, the circuitry 106 is configured to actuate the proximity sensor 110 responsive to the detected motion of the body portion. For instance, the circuitry 106 may engage the proximity sensor 110 to begin monitoring the environment for environmental objects based on motion of the body portion detected by the motion sensor 404 to aid in preventing collisions between the body portion and the environmental objects. In embodiments, the motion sensor 404 measures a speed of a movement, or relative change in speed of a movement of a body portion. For example, the system 100 can be positioned on an ankle of a subject and the motion sensor 404 measures the speed of movement of the ankle, such as one or more of a speed of movement during a flexing of the ankle during a walking motion, a speed of movement relative to a ground surface during a walking motion, or other movement. Such speed-based and acceleration-based measurements can be utilized as a reference measurement in determinations of an estimated time or force of physical impact between the body portion and an environmental object. In embodiments, the motion sensor 404 is configured to measure the disposition of the body portion over a period of time. For example, the motion sensor 404 may measure a disposition of the body portion over time while the body portion is one or more of at rest, while in motion, or while held in a position that is not a rest position (e.g., tensed). In embodiments, the motion sensor 404 is configured to measure at least one of an acceleration, a velocity, or a speed of an environmental object, which can be utilized to determine whether the environmental object is moving, even in situations where the body portion is at rest. For example, the system 100 can be configured to provide indications regarding proximity and changes in proximity when the body portion is at rest, when the body portion is in motion, when the environmental object is at rest, when the environmental object is in motion, or so forth. The measurements of the motion sensor 404 can be utilized to determine whether the environmental object will contact the body portion, including when the impact will occur. For example, the measurements of the motion sensor 404 can be utilized to determine an estimated time of impact between the body portion and the environmental object, an estimated force of impact between the body portion and the environmental object, or so forth.

In embodiments, the proximity sensor 110 includes a directional sensitivity associated with monitoring the environment, such that the proximity sensor 110 may monitor portions of the environment in proximity to the system 100, and may disregard sense signals associated with other portions, or may not scan or monitor the other portions. For example, where the system 100 is positioned on or mounted to a foot, the system 100 can monitor the environment relative to dorsal or lateral positions of the foot to search for objects that pose an impact risk to the top and sides of the foot, respectively, while disregarding or not monitoring regions below the foot, such as the floor of a room, or behind the foot. As another example, where the system 100 is positioned on or mounted to a finger, the system 100 can monitor the environment to search for objects that pose an impact risk, while disregarding to not monitoring normal finger-based interactions, such as grasping of objects, typing on a keyboard, or so forth. In embodiments, the environmental object can include a sensor configured to emit one or more signals to be received by the system 100, where the one or more signals provide a reference indication that contact with the particular object is acceptable. For example, the system 100 can disregard sense signals from the proximity sensor 110 associated with contact or impending contact with the environmental object (e.g., a keyboard, a graphical user interface, or so forth) upon receipt of the one or more signals from the environmental object associated with the reference indication that contact with the particular object is acceptable. In embodiments, the directionality of the proximity sensor 110 is attributed to one or more of a physical blockage of a portion of the proximity sensor 110, a directional facing of the proximity sensor 110 from the substrate 102, disregarding sense signals associated with directions that are not of interest, or the like. In embodiments, the system 100 can monitor posterior portions of the body portion, such as when an individual is moving backwards, such as to sit down, or maneuver about a room. In embodiments, upon monitoring the environment from a particular direction relative to the body portion, the proximity sensor 110 generates one or more sense signals associated with the proximity of the environmental object relative to the particular direction (e.g., one or more of a lateral position, a dorsal position, a posterior position, or an anterior position) from the body portion. In embodiments, the circuitry 106 is configured to instruct the reporting device 108 to generate one or more communication signals responsive to detection by the proximity sensor of the environmental object relative to the particular direction from the body portion. For instance, the reporting device 108 can be configured to report information associated with the particular directions of interest as monitored by the proximity sensor 110. As an example, the reporting device 108 can report information associated with environmental objects positioned in front of, over, to the side, behind, and so forth, while not reporting information associated with objects positioned underneath the body portion (such as the floor relative to a foot, a keyboard relative to hands or fingers, and so forth).

The circuitry 106 is configured to receive one or more sense signals from the sensor assembly 104 (e.g., sense signals from the proximity sensor 110) and to process the sense signals in order to provide control signals to portions of the system 100, such as to the reporting device 108. In embodiments, the circuitry 106 is a resident component that is coupled to the substrate 102. In embodiments, functionalities of the circuitry 106 can be performed remotely from the substrate 102, where the circuitry 106 can send and receive signals between a remote location (e.g., an external device) and the system 100 via associated wireless communication methods including, but not limited to acoustic communication signals, optical communication signals, radio communication signals, infrared communication signals, ultrasonic communication signals, and the like. The circuitry 106 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In one embodiment, the computing device includes one or more ASICs having a plurality of predefined logic components. In one embodiment, the computing device includes one or more FPGAs having a plurality of programmable logic commands.

In embodiments, the circuitry 106 is operably coupled to the sensor assembly 104 and can receive one or more sense signals generated by the sensor assembly 104 for processing of the data associated therewith. The one or more sense signals from the sensor assembly 104 can relate to a proximity of an environmental object relative to the body portion, where the sense signals can be generated by the proximity sensor 110. In embodiments, the circuitry 106 is configured to activate the reporting device 108 based on the sense signals received from the sensor assembly 104.

Figure 5:
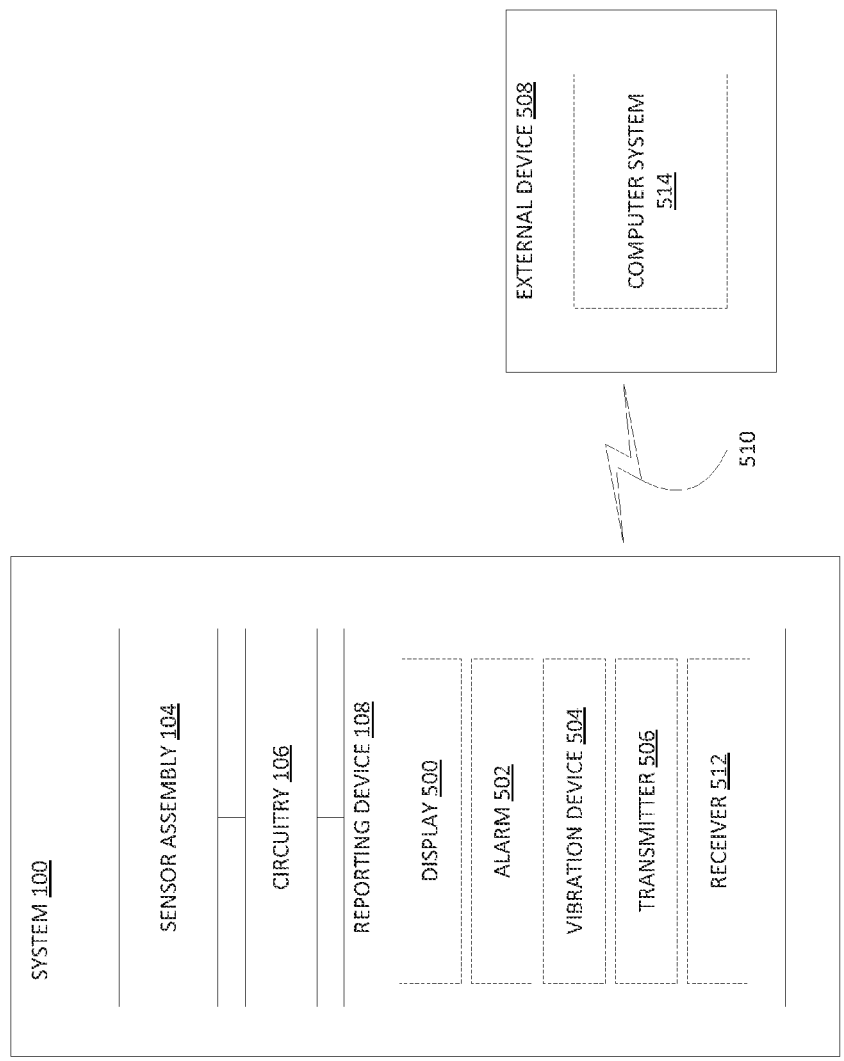
FIG. 5 is a schematic of an embodiment of a device such as shown in FIG. 1.

The reporting device 108 is configured to generate one or more communication signals to report information associated with operation of the system 100. In embodiments, the reporting device 108 is configured to generate one or more communication signals based on instruction by the circuitry 106. The information from the reporting device 108 may be provided one or more of visually (e.g., via transmission or display of visual information), audibly (e.g., via transmission or display of auditory information), tactually (e.g., via presentation of tactile information), or as data (e.g., via transmission or display of one or more data signals associated with the information to convey). The reporting device 108 may function in combination with the circuitry 106 to provide visual, auditory, or tactile information associated with detection of an environmental object in proximity to the body portion on which the system 100 is positioned or mounted. In embodiments, such as shown in FIG. 5, the reporting device 108 includes a display 500 configured to report, communicate, or otherwise provide information to a user of the system 100, such as to provide visual indications of the information associated with detection of an environmental object in proximity to the body portion, to provide recommendations to the user, such as, for example, a recommendation to move the body portion, a recommendation to check on the body portion, a recommendation to keep the body portion still, and so forth. A user may be, for example but not limited to, the subject, a care provider, a health care provider, a computing device, or a network. The display 500 may include, but is not limited to, one or more of a graphical user interface (GUI), a touchscreen assembly (e.g., a capacitive touch screen), a liquid crystal display (LCD), a light-emitting diode (LED) display, or a projection-based display. As shown in FIG. 5, the reporting device 108 can include one or more of an alarm 502, configured to provide auditory indications of the information associated with detection of an environmental object in proximity to the body portion, or a vibration device 504, configured to provide tactile indications of the information associated with detection of an environmental object in proximity to the body portion. In embodiments, the reporting device 108 includes a transmitter 506 configured to transmit information from the system 100 to an external device 508 (e.g., a remote entity, a remote device (e.g., an alarm positioned in the subject's room, a healthcare provider's room, a third party computing device, or so forth), a remote server, a remote network (e.g., a LAN (local area network), a BAN (body area network), a smart house, or so forth), an external device associated with an external network that includes one or more of a health provider network, an insurance network, a personal health record, or a personal health database, and so forth). In embodiments, the external device 508 includes a communication device, such as one or more of a mobile communication device or a computer system including, but not limited to, mobile computing devices (e.g., hand-held portable computers, Personal Digital Assistants (PDAs), laptop computers, netbook computers, tablet computers, and so forth), mobile telephone devices (e.g., cellular telephones and smartphones), devices that include functionalities associated with smartphones and tablet computers (e.g., phablets), portable game devices, portable media players, multimedia devices, satellite navigation devices (e.g., Global Positioning System (GPS) navigation devices), e-book reader devices (eReaders), Smart Television (TV) devices, surface computing devices (e.g., table top computers), Personal Computer (PC) devices, and other devices that employ touch-based human interfaces. The reporting device 108 can communicate (e.g., send and receive communication signals) with the external device 508 via one or more connected and wireless communication mechanisms (FIG. 5 displays a wireless communication mechanism 510) including, but not limited to acoustic communication signals, optical communication signals, radio communication signals, infrared communication signals, ultrasonic communication signals, and the like.

The system 100 can include a receiver, transceiver, or the like configured to receive information from an external device, an external network, or so forth. For example, as shown in FIG. 5, the reporting device 108 can include a receiver 512 configured to receive data via communication signals from the external device 108. In embodiments, the data received from the external device 108 can relate to characteristics of environmental objects including, but not limited to, proximity data, hardness data, temperature data, or the like. Such data can be utilized by the circuitry 106 for determinations related to proximity of objects relative to body portions, whether to disregard sense signals associated with detection of objects, types of responses to detection of environmental objects, or the like, as further described herein. In embodiments, the transmitter 506 is configured to transmit information to the external device 108 associated with operation of the system 100. For example, the information associated with operation of the system 100 can include, but is not limited to, time of impact between the body portion and environmental object(s), number of impacts between the body portion and environmental object(s), velocity of impact between the body portion and environmental object(s), type of environmental object(s) in contact with the body portion, or so forth.

In embodiments, the external device 508 includes a computer system 514 configured to store and execute one or more computer-executable programs, whereby the reporting device 108 can interact with (e.g., remotely access, execute, and so forth) and modify the programs stored on or accessible by the computer system 514. For example, the circuitry 106 can direct the reporting device 108 to communicate with the computer system 514, such as to transmit to the computer system 514 one or more of data associated with detection of an environmental object in proximity to the body portion, data associated with a proximity of the environmental object, data associated with a directionality of the system 100, data associated with movement of the system 100, data associated with a type of environmental object, or other information associated with operation of the system 100. In embodiments, the external device 508 receives one or more communication signals from the reporting device 108 in order to process the data stored therein. For example, the external device 508 can process one or more of data associated with detection of an environmental object in proximity to the body portion, data associated with a proximity of the environmental object, data associated with a directionality of the system 100, data associated with movement of the system 100, data associated with a type of environmental object, or other information associated with operation of the system 100. In embodiments, the external device 508 is configured to generate a response based on the data received from the reporting device 108. For example, in embodiments, the external device 508 is configured to provide one or more of a visual indication of the date, an auditory indication of the data, or a tactile indication of the data. For example, the external device 508 can be configured to illuminate a light based on detection of an environmental object in proximity to a body portion of an individual, such as a light present on the external device 508 or present in a room where the individual is located, to provide a visual indication or caution to the individual that an environmental object is in their vicinity. In embodiments, the system 100 is configured to identify particular externals devices (e.g., external device 508, a different external device, an additional external device, etc.) with which to communicate. Such external devices can depend based on an identity of the subject utilizing the system 100. For example, the system 100 can direct communications between the reporting device 108 and an external device based on identification of the subject utilizing the system 100, such as through an authentication protocol, including but not limited to, user name and password protocols, biometric identification protocols, or the like. Accordingly, the system 100 can be configured to accommodate one or more users, each of which can access information stored in the device in whole or in part based on profile settings associated with the system 100. For example, individual users can utilize the system 100 via individual or unique authentication protocols. The external device 508 can include a device that is linked to the particular subject, such as the subject's personal or professional mobile device, a mobile device of a healthcare professional that is treating the subject, or the like. The external device 508 can include a unique identifier configured to uniquely link the device with the system 100, such that the system can securely transmit data to that particular device. In embodiments, the user of the system 100 can identify which external device the system 100 is to transfer/receive data. In embodiments, the system 100 is configured to store data related to operation of the system 100, where such data can be partitioned or stored separately based on identification of the subject utilizing the system 100.

Figure 6:
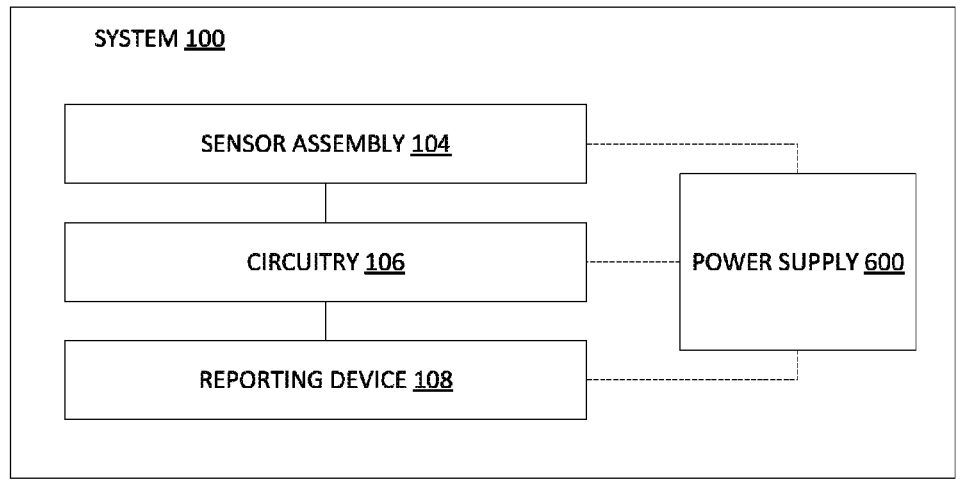
FIG. 6 is a schematic of an embodiment of a device such as shown in FIG. 1.

In embodiments, as shown in FIG. 6, the system 100 includes a power supply 600 configured to provide power to one or more components of the system 100 including, but not limited to, the sensor assembly 104, the circuitry 106, and the reporting device 108. In embodiments, the power supply 600 is a resident device component that is coupled to the substrate 102. Examples of resident device components include, but are not limited to, batteries (e.g., a thin film battery, a microbattery), solar cells (e.g., silicon-based solar cells) configured to convert light energy into electrical energy for use by the components of the system 100, and energy harvesting devices configured to generate power from motion of the body portion, motion of blood flow, and so forth. In embodiments, the power supply 600 includes one or more components positioned remotely from the substrate 102 that transmit power signals via associated wireless power methods including, but not limited to, inductive coupling of power signals. In such embodiments, the system 100 includes one or more components positioned on the substrate 102 configured to one or more of receive, process, and/or distribute the power signals that originate from components positioned remotely from the substrate 102. For example, the system 100 can include a wireless power coil coupled to the substrate 102 that is configured to receive a remote power signal, such as a remote power signal originating from a remote transmission coil (see, e.g., Kim et al., incorporated herein by reference). In embodiments, the system 100 is configured to provide an indication, via the reporting device 108 or other component, pertaining to a power level of the power supply 600. For example, the system 100 can provide an indication via the reporting device 108 regarding a power level of the supply device, including but not limited to, an indication that the power level is low (e.g., nearing depletion), an indication that the power level is depleted, an indication of the current status of the power supply, or so forth. In embodiments, the system 100 is configured to provide an indication, via the reporting device 108 or other component, pertaining to an operation status of the system 100. For example, the system 100 can provide an indication via the reporting device 108 regarding whether the system 100 is in an operational state, a non-operational state, a monitoring state, a non-monitoring state, an alarm state, a non-alarm state, or so forth.

Figure 7:
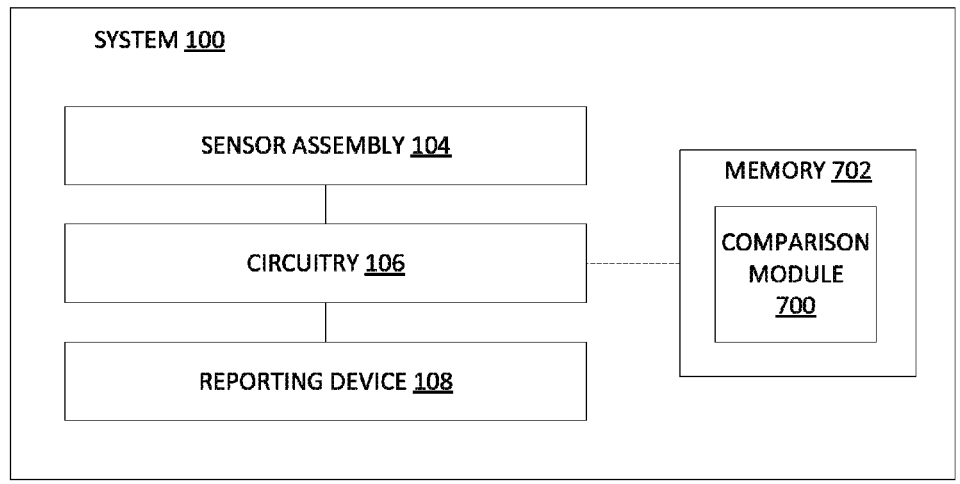
FIG. 7 is a schematic of an embodiment of a device such as shown in FIG. 1.

In embodiments, as shown in FIG. 7, the system 100 includes a comparison module 700 accessible by the circuitry 106 to identify an object sensed by the proximity sensor 110 by comparing one or more sense signals generated by the proximity sensor 110 to reference data. The reference data can include, but is not limited to data associated with one or more of characteristics of a body portion (e.g., a body portion other than the body portion on which the system 100 is positioned or mounted), reference proximity data, reference hardness data, or so forth. In embodiments, the circuitry 106 accesses the comparison module 700 by accessing a computer memory 702, which can include, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information maintained by the comparison module 700 and which can be accessed by the circuitry 106 or other associated accessing device. The reference data may be stored by the computer memory 702 of the system 100, can be accessible by the circuitry 106 via wireless means, or can be available to the circuitry 106 through another method, such as through a remote network, a cloud network, and so forth. By implementing the protocols of the comparison module 700, the circuitry 106 may compare the data obtained by the sensor assembly 104 pertaining to detection of an environmental object to reference data to determine a type of the environmental object, for example, whether the object represents a threat to injury if a physical impact were to occur, such as based on a hardness of the object. In embodiments, the circuitry 106 is configured to instruct the reporting device 108 to provide an indication of the environmental object that differs dependent on the type of object. For example, where the environmental object is determined to have a hardness that can cause injury to the body portion on impact, the circuitry 106 can instruct the reporting device 108 to provide a first indication (e.g., a light having a first color, an audible warning having a first characteristic sound, a tactile warning having a first vibration intensity, and the like). When the environmental object is determined to have a hardness that is not likely to cause injury to the body portion on impact, the circuitry 106 can instruct the reporting device 108 to provide a second indication (e.g., a light having a second color, an audible warning having a second characteristic sound, a tactile warning having a second vibration intensity, and the like), to differentiate the varying threats posed by impact with the environmental object. As one example, the circuitry 106 can instruct the reporting device to illuminate a yellow light or slight vibration upon detection of a relatively soft object, such as a pillow in proximity to the body portion, and the circuitry 106 can instruct the reporting device to illuminate a red light or more intense vibration upon detection of a relatively hard object, such as a piece of furniture in proximity to the body portion. In embodiments, the circuitry 106 is configured to instruct the reporting device 108 to provide a patterned indication regarding the environmental object. The patterned indication can vary based on proximity of an object sensed by the proximity sensor 110. For example, the indication provided by the reporting device 108 can include a light that changes color based on proximity of the object, such as changing from yellow to red as the object transitions closer to the system 100. In embodiments, the patterned indication includes an auditory indication that changes relative to the proximity of the object. For example, the indication provided by the reporting device 108 can include an audible tone that changes in intensity, frequency, or the like based on proximity of the object, such as increasing in intensity, frequency, or the like as the object transitions closer to the system 100. In embodiments, the patterned indication includes a tactile indication that changes relative to the proximity of the object. For example, the indication provided by the reporting device 108 can include a tactile indication (e.g., a vibration-based indication) that changes in intensity, frequency, or the like based on the proximity of the object, such as increasing in intensity, frequency, or the like as the object transitions closer to the system 100. By implementing the protocols of the comparison module 700, the circuitry 106 may compare the data obtained by the sensor assembly 104 pertaining to detection of an environmental object to reference data to determine a type of the environmental object, for example, to determine that the object is another body portion.

FIG. 8 illustrates a method 800 for monitoring a proximity of body portions relative to an environment in accordance with example embodiments. Method 800 shows detecting a proximity of an environmental object relative to a body portion in block 802. For example, the proximity sensor 110 of the sensor assembly 104 can detect a proximity of an environmental object relative to a body portion, such as a body portion on which the system 100 is positioned or mounted. Method 800 also includes detecting one or more of a speed, a velocity, and an acceleration of at least one of the body portion or the environmental object in block 804. For example, the sensor assembly 104 can detect a speed, a velocity, and an acceleration of the body portion, such as via the accelerometer 400, the speed sensor 402, and the motion sensor 404. Method 800 also includes determining whether the body portion or the environmental object is in motion based on one or more of the speed, the velocity, or the acceleration of the body portion or the environmental object in block 806. For example, the circuitry 106 can make a determination regarding a motion state of the body portion and/or the environmental object based on the measurements made by the sensor(s) of the sensor assembly 104. Method 800 further includes when the body portion or the environmental object is determined to be in motion, generating one or more communication signals based on detection of the proximity of the environmental object relative to the body portion in block 808. For example, the reporting device 108 can report (e.g., display, transmit) the information associated with detection of the proximity of the environmental object relative to the body portion.

FIG. 9 illustrates a method 900 for monitoring a proximity of body portions relative to an environment in accordance with example embodiments. Method 900 shows detecting a first proximity of an environmental object relative to a body portion in block 902. For example, the proximity sensor 110 of the sensor assembly 104 can detect a proximity of an environmental object relative to a body portion, such as a body portion on which the system 100 is positioned or mounted. Method 900 also includes detecting a second proximity of the environmental object relative to the body portion in block 904. For example, the proximity sensor 110 of the sensor assembly 104 can detect a proximity of the environmental object relative to the body portion, such as at a subsequent time period relative to measurement of the first proximity. Method 900 also includes determining whether the first proximity of the environmental object relative to the body portion differs from the second proximity of the environmental object relative to the body portion in block 906. For example, the circuitry 106 can make a determination regarding the first proximity and the second proximity based on the measurements made by the sensor(s) of the sensor assembly 104. Method 900 further includes when the first proximity of the environmental object relative to the body portion is determined to differ from the second proximity of the environmental object relative to the body portion, generating one or more communication signals based on detection of at least one of first proximity or the second proximity in block 908. For example, the reporting device 108 can report (e.g., display, transmit) the information associated with detection of the proximity of the environmental object relative to the body portion.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications.

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, the various embodiments described herein can be implemented, individually and/or collectively, by various types of electro-mechanical systems having a wide range of electrical components such as hardware, software, firmware, and/or virtually any combination thereof and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Examples of electro-mechanical systems include but are not limited to a variety of consumer electronics systems, medical devices, as well as other systems such as motorized transport systems, factory automation systems, security systems, and/or communication/computing systems. Electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

With respect to the use of substantially any plural and/or singular terms herein, the plural can be translated to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

This disclosure has been made with reference to various example embodiments. However, those skilled in the art will recognize that changes and modifications may be made to the embodiments without departing from the scope of the present disclosure. For example, various operational steps, as well as components for carrying out operational steps, may be implemented in alternate ways depending upon the particular application or in consideration of any number of cost functions associated with the operation of the system; e.g., one or more of the steps may be deleted, modified, or combined with other steps.

Additionally, as will be appreciated by one of ordinary skill in the art, principles of the present disclosure, including components, may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create a means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof are intended to cover a non-exclusive inclusion, such that a process, a method, an article, or an apparatus that comprises a list of elements does not include only those elements but may include other elements not expressly listed or inherent to such process, method, system, article, or apparatus.

In an embodiment, the system is integrated in such a manner that the system operates as a unique system configured specifically for function of the device 100 configured to monitor environmental conditions proximate to a body portion on which the device 100 is positioned, and any associated computing devices of the system operate as specific use computers for purposes of the claimed system, and not general use computers. In an embodiment, at least one associated computing device of the system operates as a specific use computer for purposes of the claimed system, and not a general use computer. In an embodiment, at least one of the associated computing devices of the system is hardwired with a specific ROM to instruct the at least one computing device. In an embodiment, one of skill in the art recognizes that the device 100 configured to monitor environmental conditions proximate to a body portion on which the device 100 is positioned and associated systems effect an improvement at least in the technological field of environmental sensing.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device, comprising:
   a deformable substrate configured to conform to a skin surface of a body portion;
   a sensor assembly coupled to the deformable substrate, the sensor assembly including a proximity sensor configured to generate one or more sense signals associated with a proximity of an environmental object relative to the body portion;
   circuitry operably coupled to the sensor assembly and configured to receive the one or more sense signals associated with the proximity of an environmental object relative to the body portion and to determine whether the proximity of the environmental object relative to the body portion changes over a time period; and
   a reporting device operably coupled to the circuitry and configured to generate one or more communication signals responsive to instruction by the circuitry, the one or more communication signals associated with one or more of the environmental object or a change in proximity of the environmental object relative to the body portion.

2. The device of claim 1, wherein one or more of the deformable substrate, the sensory assembly, the circuitry, or the reporting device includes at least one serpentine electronic component.

3. The device of claim 1, wherein the deformable substrate includes one or more of an elastomeric polymer, a hydrocolloid film, or a nanomembrane, wherein at least one of the sensor assembly, the circuitry, or the reporting device resides on one or more of the elastomeric polymer, the hydrocolloid film, or the nanomembrane.

4. The device of claim 1, wherein the deformable substrate includes a gas-permeable elastomeric sheet, wherein at least one of the sensor assembly, the circuitry, or the reporting device resides on the gas-permeable elastomeric sheet.

5. The device of claim 1, wherein the proximity sensor includes an optical sensor configured to detect one or more optical signals.

6. The device of claim 5, wherein the optical sensor includes at least one of a photodetector or an imaging device.

7. The device of claim 1, wherein the proximity sensor includes an acoustic sensor configured to detect one or more acoustic signals.

8. The device of claim 1, wherein the proximity sensor includes an electromagnetic proximity sensor configured to generate one or more electromagnetic signals and to detect one or more of the electromagnetic signals reflected from a surface.

9. The device of claim 1, wherein the circuitry is configured to instruct the reporting device to generate the one or more communication signals based upon the one or more sense signals generated by the proximity sensor.

10. The device of claim 1, wherein the circuitry is configured to make a determination regarding whether to instruct the reporting device to generate the one or more communication signals based upon the one or more sense signals generated by the proximity sensor.

11. The device of claim 10, wherein the circuitry includes a comparison module configured to compare the one or more sense signals generated by the proximity sensor to reference data indicative of another body portion.

12. The device of claim 11, wherein the circuitry is configured to determine not to instruct the reporting device to generate the one or more communication signals when the one or more sense signals generated by the proximity sensor indicate a presence of the other body portion.

13. The device of claim 11, wherein the circuitry is configured to instruct the reporting device to generate the one or more communication signals when the one or more sense signals generated by the proximity sensor indicate a presence of an object or surface that differs from the other body portion.

14. The device of claim 11, wherein the reference data indicative of another body portion includes at least one of reference proximity data of the other body portion or reference hardness data of the other body portion.

15. The device of claim 10, wherein the circuitry includes a comparison module configured to compare the one or more sense signals generated by the proximity sensor to reference data.

16. The device of claim 15, wherein the reference data includes hardness data associated with environmental objects.

17. The device of claim 1, wherein the sensor assembly includes a motion sensor configured to detect a movement of the body portion and to generate one or more sense signals responsive to the detection of the movement.

18. The device of claim 17, wherein the circuitry is configured to actuate the proximity sensor to generate the one or more sense signals associated with the proximity of the environmental object relative to the body portion responsive to the detection of the movement.

19. The device of claim 1, wherein the sensor assembly includes a motion sensor configured to detect at least one of an acceleration, a velocity, or a speed of the environmental object.

20. The device of claim 19, wherein the circuitry is configured to determine an estimated time of impact of the body portion with the environmental object based on the one or more sense signals generated by the proximity sensor and based on at least one of the acceleration, the velocity, or the speed of the environmental object.

21. The device of claim 19, wherein the circuitry is configured to determine an estimated force of impact of the body portion with the environmental object based on the one or more sense signals generated by the proximity sensor and based on at least one of the acceleration, the velocity, or the speed of the environmental object.

22. The device of claim 1, wherein the proximity sensor is oriented on the deformable substrate to generate one or more sense signals associated with the proximity of the environmental object relative to a particular direction from the body portion.

23. The device of claim 22, wherein circuitry is configured to instruct the reporting device to generate the one or more communication signals responsive to detection by the proximity sensor of the environmental object relative to the particular direction from the body portion.

24. The device of claim 22, wherein the circuitry is configured to disregard one or more sense signals associated with the proximity of the environmental object relative to a bottom portion of the body portion.

25. The device of claim 22, wherein the circuitry is configured to disregard one or more sense signals associated with the proximity of the environmental object relative to the particular direction from the body portion.

26. The device of claim 1, wherein the reporting device is configured to communicate with an external device.

27. The device of claim 26, wherein the reporting device is configured to receive communication signals from the external device.

28. The device of claim 26, wherein the external device is configured to provide at least one of an auditory indication pertaining to the one or more sense signals associated with one or more of the environmental object or the change proximity of the environmental object relative to the body portion, a visual indication pertaining to the one or more sense signals associated with one or more of the environmental object or the change proximity of the environmental object relative to the body portion, or a tactile indication pertaining to the one or more sense signals associated with one or more of the environmental object or the change in proximity of the environmental object relative to the body portion, responsive to the one or more communication signals from the reporting device.

29. The device of claim 1, wherein the reporting device is configured to communicate with an external network.

30. The device of claim 29, wherein the external network includes one or more of a health provider network, an insurance network, a personal health record, or a personal health database.

31. The device of claim 1, further including a power supply configured to supply power to one or more of the sensor assembly, the circuitry, or the reporting device.

32. The device of claim 31, wherein the power supply includes at least one of a battery coupled to the deformable substrate, a thin film battery coupled to the deformable substrate, a microbattery coupled to the deformable substrate, one or more wireless power coils configured to receive a remote power signal, one or more inductive coils configured to receive a remote power signal from a transmission coil, a solar cell coupled to the deformable substrate, or an energy harvesting device configured to generate power from motion of the body portion.

33. The device of claim 1, wherein the sensor assembly includes at least one of an accelerometer configured to measure an acceleration of the body portion or a speed sensor configured to measure one or more of a speed or a velocity of the body portion.

34. The device of claim 33, wherein the circuitry is configured to at least one of actuate the proximity sensor to generate the one or more sense signals responsive to the acceleration of the body portion, determine an estimated time of impact of the body portion with the environmental object based on the one or more sense signals generated by the proximity sensor and based on the acceleration of the body portion, determine an estimated force of impact of the body portion with the environmental object based on the one or more sense signals generated by the proximity sensor and based on the acceleration of the body portion, actuate the proximity sensor to generate the one or more sense signals responsive to one or more of the speed or the velocity of the body portion, instruct the reporting device to generate the one or more communication signals responsive to one or more of the speed or the velocity of the body portion, determine an estimated time of impact of the body portion with the environmental object based on the one or more sense signals generated by the proximity sensor and based on one or more of the speed or the velocity of the body portion, or determine an estimated force of impact of the body portion with the environmental object based on the one or more sense signals generated by the proximity sensor and based on one or more of the speed or the velocity of the body portion.

35. The device of claim 1, wherein the reporting device is configured to provide at least one of an auditory indication pertaining to the one or more sense signals associated with one or more of the environmental object or the change in proximity of the environmental object relative to the body portion, a visual indication pertaining to the one or more sense signals associated with one or more of the environmental object or the change in proximity of the environmental object relative to the body portion, or a tactile indication pertaining to the one or more sense signals associated with one or more of the environmental object or the change in proximity of the environmental object relative to the body portion.

36. The device of claim 1, wherein the body portion includes at least one of a finger, a hand, a wrist, a toe, a foot, an ankle, an arm, an elbow, a leg, a knee, a shoulder, or a hip.

37. A method, comprising:
detecting, via an epidermal electronic system (EES) located on a body portion of an individual, a first proximity of an environmental object relative to the body portion;
generating one or more sense signals based on detection of the first proximity of the environmental object relative to the body portion;
detecting, via the epidermal electronic system (EES) located on the body portion of the individual, a second proximity of the environmental object relative to the body portion;
generating one or more sense signals based on detection of the second proximity of the environmental object relative to the body portion;
determining whether the first proximity of the environmental object relative to the body portion differs from the second proximity of the environmental object relative to the body portion; and
when the first proximity of the environmental object relative to the body portion is determined to differ from the second proximity of the environmental object relative to the body portion, generating one or more communication signals based on detection of at least one of the first proximity or the second proximity.

38. The method of claim 37, wherein detecting, via an epidermal electronic system (EES) located on a body portion of an individual, a first proximity of an environmental object relative to the body portion includes:
detecting, via the epidermal electronic system (EES) located on the body portion of the individual, one or more optical signals associated with the first proximity of the environmental object relative to the body portion.

39. The method of claim 37, wherein detecting, via an epidermal electronic system (EES) located on a body portion of an individual, a first proximity of an environmental object relative to the body portion includes:
detecting, via the epidermal electronic system (EES) located on the body portion of the individual, one or more acoustic signals associated with the first proximity of the environmental object relative to the body portion.

40. The method of claim 37, wherein detecting, via an epidermal electronic system (EES) located on a body portion of an individual, a first proximity of an environmental object relative to the body portion includes:
detecting, via the epidermal electronic system (EES) located on the body portion of the individual, one or more electromagnetic signals reflected from a surface of the environmental object.

41. The method of claim 37, further including:
comparing at least one of the one or more sense signals based on detection of the first proximity or the one or more sense signals based on detection of the second proximity to reference data indicative of another body portion.

42. The method of claim 41, wherein the reference data indicative of another body portion includes at least one of reference proximity data of the other body portion or reference hardness data of the other body portion.

43. The method of claim 37, further including:
determining an estimated time of impact of the body portion with the environmental object based on the one or more sense signals based on detection of the first proximity and the one or more sense signals based on detection of the second proximity.

44. The method of claim 37, further including:
determining an estimated force of impact of the body portion with the environmental object based on the one or more sense signals based on detection of the first proximity and the one or more sense signals based on detection of the second proximity.

45. The method of claim 37, wherein detecting, via an epidermal electronic system (EES) located on a body portion of an individual, a first proximity of an environmental object relative to the body portion includes:
detecting, via the epidermal electronic system (EES) located on the body portion of the individual, the first proximity of the environmental object relative a particular direction from the body portion.

46. The method of claim 45, wherein detecting, via the epidermal electronic system (EES) located on the body portion of the individual, the first proximity of the environmental object relative a particular direction from the body portion includes:
detecting, via the epidermal electronic system (EES) located on the body portion of the individual, the first proximity of the environmental object relative a lateral portion of the body portion.

47. The method of claim 45, wherein detecting, via the epidermal electronic system (EES) located on the body portion of the individual, the proximity of the environmental object relative a particular direction from the body portion includes:
detecting, via the epidermal electronic system (EES) located on the body portion of the individual, the proximity of the environmental object relative a dorsal portion of the body portion.

48. The method of claim 37, further including:
transmitting the one or more communication signals to an external device.

49. The method of claim 37, wherein generating one or more communication signals based on detection of at least one of the first proximity or the second proximity includes:
providing at least one of an auditory indication pertaining to the one or more sense signals based on detection of at least one of the first proximity or the second proximity, a visual indication pertaining to the one or more sense signals based on detection of at least one of the first proximity or the second proximity, a tactile indication pertaining to the one or more sense signals based on detection of at least one of the first proximity or the second proximity.

50. A system, comprising:
a device, including:
a deformable substrate configured to conform to a skin surface of a body portion;
a sensor assembly coupled to the deformable substrate, the sensor assembly including a proximity sensor configured to generate one or more sense signals associated with a proximity of an environmental object relative to the body portion;
circuitry operably coupled to the sensor assembly and configured to receive the one or more sense signals associated with the proximity of an environmental object relative to the body portion and to determine whether the proximity of the environmental object relative to the body portion changes over a time period; and
a reporting device operably coupled to the circuitry and configured to generate one or more communication signals responsive to instruction by the circuitry, the one or more communication signals associated with one or more of the environmental object or a change in proximity of the environmental object relative to the body portion; and
an external device communicatively coupled with the device, the external device configured to at least one of receive the one or more communication signals from the device or transmit one or more communication signals associated with environmental object characteristics to the device.

* * * * *